United States Patent [19]

Norman

[11] Patent Number: 5,187,300

[45] Date of Patent: Feb. 16, 1993

[54] VOLATILE PRECURSORS FOR COPPER CVD

[75] Inventor: John A. T. Norman, Encinitas, Calif.

[73] Assignee: Air Products and Chemicals, Inc., Allentown, Pa.

[21] Appl. No.: 764,566

[22] Filed: Sep. 20, 1991

Related U.S. Application Data

[63] Continuation-in-part of Ser. No. 650,332, Feb. 4, 1991, Pat. No. 5,085,731.

[51] Int. Cl.$^5$ .............................. C07F 1/08; C07F 7/08
[52] U.S. Cl. ........................................ 556/12; 556/113
[58] Field of Search ................................ 556/12, 113

[56] References Cited

U.S. PATENT DOCUMENTS 3,356,527 2/1967 Moshier et al. .................. 117/107.2
3,594,216 7/1971 Charles et al. .................... 117/107.2
4,425,281 1/1984 Doyle ................................. 260/430

OTHER PUBLICATIONS

Jain et al., Chem. Mater., vol. 3, No. 6, pp. 995-997 (1991).
Chi et al., Inorganic Chemistry, vol. 30, No. 23, pp. 4293-4294 (1991).
T. Ohba, et al, "Deposition and Properties of Blanket-W Using Silane Reduction", ed. by S. S. Wong, Mat. Res. Soc. Symp., Pittsburgh, Penna. (1990).
T. Ohba, et al. "Selective CVD Tungsten Silicide for VLSI Applications", Tech. Dig. IEDM 213 (1987).
R. L. Van Hemert, "Vapor Deposition of Metals by Hydrogen Reduction of Metal Chelates", J. Electrochem. Soc., vol. 112, No. 11, p. 1123 (1965).
D. Temple and A. Leisman, "Chemical Vapor Deposition of Copper from Copper(11) Hexafluoroacetylacetonate", J. Electrochem. Soc., vol. 136, No. 11, Nov. ((1989).
A. C. Kaloyers, et al, "Low-Temperature Metal-Organic Chemical Vapor Deposition (LTMOCVD) of Device-Quality Copper Films for Microelectronic Applications", J. Electronic Mat., vol. 19, No. 3 (1990).
C. Oehr, et al., "Thin Copper Films by Plasma CVD Using Copper-Hexafluoro-Acetylacetonate," Appl. Phys. A 45, 151-154 (1988).
F. A. Houle, et al., "Laser Chemical Vapor Deposition of Copper", Appl. Phys. Lett. 46(2), pp. 204-206 Jan. (1985).
F. A. Houle, et al., "Surface Processes Leading to Carbon Contamination of Photochemically Deposited Copper Films", J. Vac. Sci. Technol. A 4(6) p. 2452, (1986).
P. M. Jeffries and G. S. Girolami, "Chemical Vapor Deposition of Copper and Copper Oxide Thin Films from Copper(1) tert-Butoxide", Chem. of Materials, (1), pp. 8-10, (1989).
D. B. Beach, et al., "Ion-Temperature Chemical Vapor Deposition of High-Purity Copper From an Organometallic Source", Chem. Mater. (2), pp. 216-219, (1990).

Primary Examiner—José G. Dees
Assistant Examiner—Porfirio Nazario-Gonzalez
Attorney, Agent, or Firm—Mark L. Rodgers; William F. Marsh; James C. Simmons

[57] ABSTRACT

Volatile liquid or low melting solid organometallic copper complexes are provided which are capable of selectively depositing a copper film onto metallic or other electrically conducting portions of a substrate surface under CVD conditions. These organometallic copper complexes are represented by the structural formula:

$$Cu^{+1}(R^1-\underset{\underset{O}{\|}}{C}-\underset{\underset{R^2}{|}}{C}-\underset{\underset{O}{\|}}{C}-R^3)^{-1} \cdot R^4-C\equiv C-Si(R^5)_3$$

wherein $R^1$ and $R^3$ are each independently $C_1$-$C_8$ perfluoroalkyl, $R^2$ is H, F or $C_1$-$C_8$ perfluoroalkyl, $R^4$ is $C_1$-$C_8$ alkyl, phenyl, or $Si(R^5)_3$, and each $R^5$ is independently $C_1$-$C_8$ alkyl or phenyl. A process for depositing copper films using these organometallic copper complexes is also provided.

7 Claims, No Drawings

VOLATILE PRECURSORS FOR COPPER CVD

CROSS REFERENCE TO PARENT APPLICATION

This application is a continuation-in-part of co-pending application Ser. No. 07/650,332, filed Feb. 4, 1991, now U.S. Pat. No. 5,085,731.

TECHNICAL FIELD OF THE INVENTION

The present invention relates to complexes useful for the deposition of copper films onto conducting metallic or metallic-like surfaces.

BACKGROUND OF THE INVENTION

In the electronics industry there is a steady trend towards manufacturing microprocessors of increasingly high speed and large information storage capacity. This requires the individual electrical devices such as transistors, etc. within the microprocessors to be fabricated at an increasingly small scale. The metallic electrical interconnects between the devices also need to be miniaturized. As device and interconnect dimensions approach one-half to one-quarter of a micron, the choice of interconnect metal becomes critical. The large current densities resulting from small interconnect cross sectional areas can lead to major problems such as electromigration, stress migration, and voiding where the metal lines become fractured or otherwise physically degraded under operating conditions, a major drawback with aluminum alloys. Metal interconnects also need to provide the lowest electrical resistance path possible since resistance-capacitance delays become a dominant factor in circuit performance at sub half micron levels. The aluminum that is widely used in present day interconnect manufacturing is reasonably conductive (2.7 microhm cm), but needs to be alloyed with 0.5 to 4.0% Cu to minimize the electromigration tendencies of the pure metal. Tungsten, also widely used, is electromigration resistant but is of higher resistivity (5.4 microhm cm). Considering these facts, copper should be an excellent interconnect metal as it is both highly conductive (1.7 microhm cm) and electromigration resistant.

Metallic interconnects are typically horizontal lines (runners) or plugs (vias) that wire together devices in microprocessors. At feature sizes of >1 micron these metallic components can be built into the microcircuits by PVD (Physical Vapor Deposition) techniques such as sputtering or evaporation. In essence PVD consists of condensing a metal vapor onto a surface or into a hole or channel of a circuit where an electrical connection needs to be formed. Since this is a non-selective metallization, either a postdeposition clean-up (i.e. etchback) or a predeposition masking of the substrate (i.e. the lift-off technique) is required in order to prepare individual discreet metal components. However, the severe surface topographies presented by sub-micron features preclude the effective use of PVD since this "line of sight" technique cannot provide a uniform conformal coating on such high aspect ratio highly convoluted surfaces. Specific examples of these shortcomings include the phenomena of geometrical shadowing and poor step coverage.

A superior process for producing these microscopic metal features is CVD (Chemical Vapor Deposition). In this technique a volatile metal-organic compound in the gas phase is contacted with areas of a circuit where growth of a metal film (i.e. interconnect) is required. A surface catalyzed chemical reaction then occurs which leads to deposition of the desired metal. Since this is a chemical reaction, there is potential for it to provide surface selective metallization. That is, CVD metal deposition can be made to occur at only specific locations compared to the non-selective PVD processes. Also, since the metal film steadily grows on the desired surface it is of a uniform thickness and highly conformal even to severe geometries. In this respect CVD is naturally suited to fabricating submicron high aspect ratio features.

An example of selective CVD metallization that is currently commercially practiced is the deposition of tungsten onto a silicon surface using tungsten hexafluoride as the volatile organometallic precursor (see T. Ohba, et al., "Tungsten and Other Advanced Metals for VLSI/ULSI Applications V," Ed. by S. S. Wong and S. Furukawa, MRS, Pittsburgh, Pa., 273 (1990)). The chemistry that drives this process can be divided into two steps. Initially the $WF_6$ reacts with the elemental silicon surface to yield tungsten metal and volatile silicon hexafluoride. Hydrogen gas is then added to the system which reduces further $WF_6$ at the freshly formed metal surface thereby yielding additional tungsten and HF gas. Although this system currently enjoys widespread use as the only "selective" CVD metallization process that is widely commercially available, loss of selectivity can be observed and is commonly ascribed to the corrosive nature of HF. T. Ohba, et al., Tech. Dig. IEDM, 213 (1987) teach the use of silane as a reducing agent for $WF_6$ to achieve higher deposition rates while avoiding the production of HF gas.

Desirable selectivities for a copper CVD process include deposition onto conducting metallic or metallic like surfaces such as tungsten, tantalum, titanium nitride or platinum silicide versus insulating surfaces such as silicon oxide. These metallic surfaces provide a diffusion barrier between the CVD copper and the underlying silicon substrate that the device is grown upon.

Copper films have previously been prepared via CVD using various copper precursors. Most of these compounds will only deposit copper metal at temperatures higher than 200° C. with no significant selectivity between substrates such as diffusion barrier surfaces vs. silicon oxide. The best known and most frequently used CVD copper precursor is the solid compound copper$^{+2}$ bis(hexafluoroacetylacetonate). This highly fluorinated organometallic precursor is significantly more volatile than its parent unfluorinated complex copper$^{+2}$ bis(acetylacetonate) and its ease of vaporization readily lends this compound towards CVD processes. The use of this compound as a general precursor for CVD copper metallization was first described by R. L. Van Hemert et al. J. Electrochem. Soc. (112), 1123 (1965) and by R. W. Moshier et al. U.S. Pat. No. 3,356,527. More recently Reisman, et al., J. Electrochemical Soc., Vol. 136, No. 11, November 1989 and A. E. Kaloyeros et al. Journal of Electronic Materials, Vol. 19, No. 3, 271 (1990) in two independent studies have also evaluated the use of this compound as a copper precursor for electronics applications. In these studies copper films were formed by contacting vapors of copper$^{+2}$(hfac)$_2$, mixed with either an inert gas (argon) or with hydrogen and contacting the mixture with a heated substrate surface. In the case of using hydrogen the copper$^{+2}$ atom in the precursor complex is formally reduced to copper metal while the hfac$^{-1}$ ligand becomes protonated to yield a neutral volatile compound. In the case of using an inert gas the copper$^{+2}$(hfac)$_2$ is simply pyrolyzed to give copper metal and fragments of the hfac ligand.

Pure copper is reported for the hydrogen reduction but oxygen and carbon are found in the films obtained by pyrolysis. However, the lowest deposition temperatures for either process is 250° C. and no strong selectivities towards metallic vs. silicon oxide surfaces are reported. Copper films have also been prepared from copper$^{+2}$(hfac)$_2$ by plasma enhanced deposition, C. Oehr, H. Suhr, Appl. Phy. A. (45) 151-154 (1988), laser photothermal decomposition, F. A. Houle; C. R. Jones; T. Baum; C. Pico; C. A. Korae; *Appl. Phys. Lett.* (46) 204-206 (1985), and photochemical decomposition of copper$^{+2}$(hfac)$_2$ ethanol adducts, F. A. Houle; R. J. Wilson; T. H. Baum; *J. Vac. Sci. Technol.* A (4), 2452-2458 (1986). Some of these methods yield fluorine contaminated films and none are reported to yield selective depositions. Similar hydrogen reduction of volatile copper compounds has also been demonstrated by Charles et al. U.S. Pat. No. 3,594,216 using copper$^{+2}$ β-ketoimine complexes at 400° C. to deposit copper metal films onto glass or quartz substrates. No mention of selectivity is made. G. S. Girolami, et al., *Chem. Mater.* (1) 8-10 (1989) reported using solid copper$^{+1}$ t-butoxide to yield copper films by CVD at 400° C., but the resultant films were impure in that they contained 5% oxygen.

The only CVD precursors known to deposit pure copper metal films below 200° C. are the copper$^{+1}$ cyclopentadienyl phosphine compounds described by Beech et al., *Chem. Mater.* (2) 216-219 (1990), but these are also not reported to be strongly selective towards metallic or metallic like surfaces vs. silicon oxide or similar insulating dielectrics. An additional problem that this particular class of compounds faces for electronics applications is their potential to contaminate microcircuits with phosphorus, an element that is extensively used as a silicon dopant.

Doyle, U.S. Pat. No. 4,425,281 discloses Cu(I) complexes containing fluorinated acetylacetonate anions and unsaturated hydrocarbons as ligands, which complexes are taught to be useful as catalysts or catalyst precursors.

SUMMARY OF THE INVENTION

The present invention is a class of volatile liquid or low melting solid organometallic copper complexes which are capable of selectively depositing a copper film onto metallic or other electrically conducting portions of a substrate surface under CVD conditions. These organometallic copper complexes are represented by the structural formula:

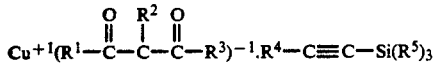

wherein $R^1$ and $R^3$ are each independently $C_1$-$C_8$ perfluoroalkyl, $R^2$ is H, F or $C_1$-$C_8$ perfluoroalkyl, $R^4$ is $C_1$-$C_8$ alkyl, phenyl, or Si($R^5$)$_3$, and each $R^5$ is independently $C_1$-$C_8$ alkyl or phenyl. Additionally, the present invention is also a CVD process for selectively depositing copper films using these organometallic copper complexes.

The above compounds have been found to be either distillable liquids or volatile low melting solids which exhibit excellent properties as CVD precursors; such as the ability to selectively deposit copper onto metallic or other electrically conducting portions of a substrate surface to the exclusion of deposition onto silicon oxide or other similar non-conducting (i.e. insulating) surfaces. Unlike typical prior art CVD copper precursors, the complexes of the present invention are liquid under ambient or slightly warmer than ambient conditions which allows them to be utilized in standard "bubbler" precursor delivery systems that are widely used in the electronics industry.

DETAILED DESCRIPTION OF THE INVENTION

The present invention is an improved class of liquid or low melting solid CVD precursors which are capable of selectively depositing pure, thin copper films on metallic or other electrically conducting portions of a substrate surface. These precursors are organometallic copper complexes, and more specifically, copper$^{+1}$(β-diketonate).silylalkyne complexes wherein the silylalkyne is a stabilizing ligand composed in part of a silicon atom connected to an acetylinic triple bond. These organometallic copper complexes can be represented by the structural formula:

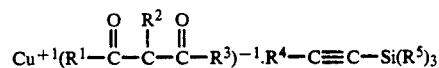

wherein $R^1$ and $R^3$ are each independently $C_1$-$C_8$ perfluoroalkyl, $R^2$ is H, F or $C_1$-$C_8$ perfluoroalkyl, $R^4$ is $C_1$-$C_8$ alkyl, phenyl, or Si($R^5$)$_3$, and each $R^5$ is independently $C_1$-$C_8$ alkyl or phenyl.

We have found these complexes to be either distillable liquids or low melting volatile solids which exhibit excellent properties as CVD precursors for the selective deposition of copper onto metallic or other electrically conducting portions of a substrate surface while avoiding deposition on silicon oxide or other insulating (i.e. non-conductive) portions of the surface. Such metallic or other electrically conducting surfaces include: Ti, Ta, Al, and the like. The deposition conditions are those typically employed in conventional low pressure CVD applications, with the exception that, in addition to conventional CVD temperatures, the present process allows for lower deposition temperatures to be used, i.e., between 200° C. and 300° C.

While not intending to be bound by theory, it is believed that as CVD precursors, these compounds function by a surface catalyzed disproportionation to give a volatile Cu$^{+2}$ complex, free substituted silylalkyne and copper metal. For the precursors to be useful it is essential that the alkyne is bound strongly enough to permit vaporization without extensive decomposition, yet weakly enough at elevated temperatures to permit disproportionation and copper deposition to occur, as in the CVD process. A possible mechanism is represented below for the volatile liquid complex copper$^{+1}$hfac.TMSP (hfac being an abbreviation for the hexafluoroacetylacetonate anion and TMSP being an abreviation for trimethylsilylpropyne). Both the TMSP and the Cu$^{+2}$(hfac)$_2$ are volatile byproducts; (s) denotes interaction with a surface and (g) denotes the gas phase.

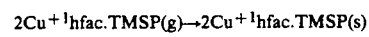     1.

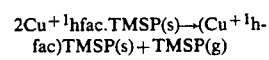     2.

$$(Cu^{+1}hfac)_2 TMSP(s) \rightarrow 2Cu^{+1}hfac(s) + TMSP(g) \quad 3.$$

$$2Cu^{+1}hfac(s) \rightarrow Cu(s) + Cu^{+2}(hfac)_2(g) \quad 4.$$

In step 1, the complex is absorbed from the gas phase onto a metallic surface. In step 2, one molecule of TMSP dissociates from one molecule of $Cu^I hfac.TMSP$ and the resulting $Cu^I hfac$ then shares the TMSP of an adjacent $Cu^I hfac.TMSP$ to form $(Cu^I hfac)_2.TMSP$. In step 3, TMSP dissociates from $(Cu^I hfac)_2.TMSP$ leaving behind $Cu^{+1}hfac$ as an unstable compound. In step 3, the $Cu^{+1}hfac$ disproportionates to yield copper metal and volatile $Cu^{+2}(hfac)_2$.

The disproportionation at CVD temperatures appears to be most strongly catalyzed by metallic or electrically conducting surfaces thereby providing the system with a selectivity that is very attractive from a microelectronics processing perspective.

The present organometallic complexes have the ability to selectively deposit copper films from 200° C. to 300° C., without significantly compromising the growth rate of the film. The ability to deposit copper at these low temperatures is especially important for the so called upper-level metals in multi-metal layer ICs as excessive heat is to be avoided during the later stages of microprocessor fabrication to prevent thermally induced inter-diffusion of layer materials and dopants at device interfaces. Also, as stated above, because these complexes are liquids or low melting solids under ambient or near ambient conditions they can be utilized in standard CVD "bubbler" precursor delivery systems currently used in the electronics industry.

An additional advantage of the silylalkyne based series of compounds described in this disclosure is that they can be readily stabilized against disproportionation at elevated temperatures in both the liquid and gas phase under CVD conditions due to the fact that the metal center of a $Cu+1(hfac).silyl-alkyne$ is coordinately saturated. A silylalkyne or other 4 electron donating ligand capable of coordinately saturating and stabilizing a copper+1(hfac) complex can be introduced into the source sweep gas thus suppressing both dissociation of alkyne from the copper complex and its subsequent disproportionation. This is shown below in equation 1. That is, the equilibrium shown is driven to the left hand side by the addition of free silylalkyne. Additional silylalkyne cannot coordinate to form a less volatile bis(silylalkyne) complex as shown in equation 2. This is in contrast to the previously described $Cu+1(hfac).silylolefin$ series of compounds where an analogous addition of free silylalkene can lead to the formation of a less volatile $Cu+1(hfac).(silylolefin)2$ compound as shown in equation 3.

$$Cu+1(hfac).silylalkyne \rightleftharpoons Cu+1(hfac) + silylalkyne \quad 1/$$

$$Cu+1(hfac).silylalkyne + silylalkyne^* > Cu+1(hfac)(silylalkyne)2 \quad 2/$$

$$Cu+1(hfac).silylolefin + silylolefin \rightarrow Cu+1(hfac)\text{-}(silylolefin)2 \quad 3/$$

We have also shown that under conditions of vacuum transfer (i.e. application of heat and vacuum) two molecules of a volatile $Cu+1(hfac).silylalkyne$ complex can lose one molecule of silylalkyne to form a new volatile 2:1 compound where two copper metal centers share one silylalkyne. This reaction is reversible since the addition of free silylalkyne to the 2:1 compound restores it back to the original complex. This reversible reaction is shown in equation 4.

$$2Cu+1(hfac).silylalkyne \rightleftharpoons [Cu+1(hfac)]2.silylalkyne + silylalkyne \quad 4/$$

Therefore the reaction to the right hand side can also be suppressed by the addition of free silylalkyne in the same way that disproportionation is suppressed as explained through equations 1 and 2 above. Thus complete control over the chemical stability of the $Cu+1(hfac).silylalkyne$ complex as it is used in a CVD system is achieved by the controlled addition of free silylalkyne.

Additionally, the present process is advantageous in that it does not result in the release of corrosive or otherwise detrimental byproducts that can lead to a loss of selectivity or damage to the microprocessor substrate.

In an additional embodiment, hydrogen can be used in the CVD reduction of the organometallic copper complexes of the present invention to yield metallic copper in a similar manner that it is reported to reduce $Cu^{+2}(hfac)_2$. This more effectively utilizes the precursor from the perspective that each metal center would yield metallic copper in contrast to the disproportionation reaction where only ½ of the initial $Cu^{+1}$ centers yield copper metal. In instances in which this results in the loss of selectivity, an initial selective deposition in the absence of hydrogen can be utilized to deposit a seed layer of copper which would then be grown by subsequent CVD processing by hydrogen reduction. Optionally, other reducing gases could also be used.

It is believed, based upon what has previously been observed for silylolefin complexes, that the present CVD reaction can be reversed such that copper metal deposited via a blanket deposition reaction can be removed, i.e., etched from the metallic surface area of a substrate. In accordance with this technique, a copper (+2) complex along with a suitable silylalkyne, both in the vapor phase, are brought into contact with a substrate onto which excess copper has been deposited. The copper metal on the surface of the substrate is converted into a volatile copper (+1) complex and is evaporated away from the metal surface. The general chemical equation for this etching reaction is as follows:

$$Cu^\circ + Cu^{+2}(ligand)_2 + 2silylalkyne \rightarrow 2Cu^{+1}\text{-}(ligand).silylalkyne$$

Suitable ligands and silylalkyne for this reaction correspond to those of the metal complex precursors set out above. Prior to the present invention, known etching processes were inappropriate for copper since prior processes resulted in the generation of copper halides which are involatile and were left behind as surface contaminants.

EXPERIMENTAL

In the following examples, temperatures are set forth uncorrected in degrees celcius. Unless otherwise noted, all parts and percentages are by weight. 1,1,1,5,5,5-hexafluoro-2,4-pentanedione was purchased from Fairfield Chemical Company, Blythewood, SC. Trimethylsilylpropyne, bis(trimethylsilyl)acetylene, copper chloride and potassium hydride were purchased from Aldrich Chemical Co., Milwaukee WI. Diethylmethylvinylsilane was purchased from Huls, Piscataway, NJ. HPLC grade terahydrofuran (THF) and HPLC grade hexane were distilled from sodium benzophenone under an atmosphere of nitrogen prior prior to use. All operations in the preparation of metal complexes were carried out using standard Schlenk line techniques as described by D. F. Shriver in the "Manipulations of Air Sensitive Compounds" McGraw-Hill Publishing Co. $^1H$ $^{13}C$ and $^{19}F$ NMR were recorded using Bruker ACP-300 and SY-200 spectrometers.

EXAMPLE 1

Synthesis of Cu+1(hfac).trimethylsilylpropyne (i.e. Cu+1hfac.TMSP)

Under an atmosphere of nitrogen 0.178 moles of 1,1,1,5,5,5-hexafluoro-2,4-pentanediole were slowly added over 30 minutes to 0.178 g of potassium hydride stirring in 150 ml of THF at room temperature. Hydrogen gas was evolved and slight warming of the reaction occurred. The resultant solution was then transferred under nitrogen to another flask containing 0.178 moles of cuprous chloride and 0.178 g of trimethylsilyl propyne stirring in 150 ml of THF. The resultant mixture was then stirred at 60° C. for 2 hours during which time it was observed to turn a deep yellow color. Filtration under nitrogen followed by evaporation of THF from the filtrate yielded a yellow crude reaction product. This was suspended in 100 ml of hexane, refiltered under nitrogen and the hexane evaporated to yield a yellow liquid. Purification of the liquid complex could be achieved by a bulb-to-bulb distillation. Yield=58%. NMR: (deuterobenzene) δ0.26(S,9H); δ1.7(S,3H); δ6.19 (S,1H).

EXAMPLE 2

Synthesis of Cu+1(hfac).bis(trimethylsilyl)acetylene (i.e., Cu'hfac)BTMSA

The above synthesis shown in Example 1 was repeated but substituting an equivalent quantity of bis(-trimethylsilyl)acetylene for trimethylsilylpropyne. The final product was isolated as a yellow crystalline solid, mp 50° C. Yield=86%. NMR: (deuterobenzene) δ0.30(S,18H); δ6.14(S,1H).

COPPER DEPOSITION BY CVD

The selectivity of deposition from these silylalkyne stabilized Cu+1(hfac) compounds was demonstrated using Cu+1(hfac).BTMSP as follows: One quarter fragments ("test wafers") of metallized 4" silicon wafers, for example titanium on silicon or patterened aluminum and silicon dioxide on silicon were simultaneously exposed to the same CVD conditions for the deposition of copper. In each case a strong selectivity towards the metallic surface was observed in the form of an adherent thick copper film forming upon it compared to little or no copper deposition on the silicon oxide. Selectivity was determined by visual inspection of the test wafers at 200–1000X using an optical microscope. All of the films were found to be highly adherent by their resisting being lifted from their substrate surfaces by the application and subsequent removal of 3M ® Scotch ® tape. The resistivity of the deposited copper was determined to be approximately 2.0 microohm cm.

The depositions for examples 3, 4 and 5 listed below were carried out as follows: vapors of Cu+1(hfac).BTMSA were fed into a cold wall stainless steel single wafer CVD reactor by means of bubbling nitrogen gas at approximately 2.5 torr through a source of the complex set at 60° C. Inside the reactor the vapors of the copper precursor contacted a resistively heated stainless steel pedestal bearing a copper plate upon which the test wafers were heated to be the predetermined deposition temperature. The actual temperature of a given test wafer was measured via a thermocouple contacting the topside of the wafer. Each run was started by first loading the test wafers into the load lock chamber and subsequently pumping the chamber down to 10 mtorr pressure. The load lock was connected to the deposition chamber by a slit valve. After pumpdown of the load lock the slit valve was opened and the sample transferred from the load lock into the reaction chamber via a robotic arm. The arm was withdrawn after it had placed the test wafers upon the heated copper plate standing on top of the stainless steel pedestal. The slit valve was then closed to isolate the chamber. The samples were brought to deposition temperature under a flowing nitrogen ambient. The system was then pumped to less than 10 mtorr, the source maintained at 60° C. was then opened to the chamber and nitrogen carrier gas was bubbled through it for a predetermined time. During the deposition a pressure control system maintained the desired reaction pressure. The deposition ceased when the carrier gas was turned off and the source closed. The chamber was evacuated to less than 10 mtorr, then flushed with nitrogen and re-evacuated. This was repeated. The wafer was then drawn back into the load lock chamber via the robotic arm, the slit valve was closed thus isolating the load lock chamber and the wafer allowed to cool under nitrogen to prevent oxidation of the deposited copper film.

CVD RESULTS

For all of the results listed below, source temp=60° C., vapor pressure of Cu+1(hfac)BTMSA=0.4 torr, nitrogen carrier gas bubbled at 20 sccm.

| Example | Coupon Temp. | CVD Chamber Pressure | Mass Transfer Rate of Copper Source | Deposition |
| --- | --- | --- | --- | --- |
| 3 | 210° C. | 750 mt | 3.5 sccm | deposited on Cu, Al not SiO$_2$ or Ti |
| 4 | 260° C. | 500 mt | 3.5 sccm | deposited on Cu, Al and Ti not on SiO$_2$ |
| 5 | 240° C. | 140 m | 3.5 sccm | deposited on Cu, Al, Ti not on SiO$_2$ |

Average deposition rate for examples 3, 4 and 5 was 400 Å/min.

What is claimed is:

1. A volatile liquid or low melting volatile solid organometallic copper complex capable of selectively depositing a copper film onto metallic or other electrically conducting portions of a substrate surface under CVD conditions, said complex having the structural formula:

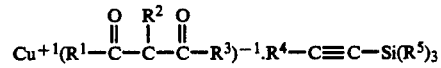

wherein $R^1$ and $R^3$ are each independently $C_1$-$C_8$ perfluoroalkyl, $R^2$ is H, F or $C_1$-$C_8$ perfluoroalkyl, $R^4$ is $C_1$-$C_8$ alkyl, phenyl, or $Si(R^5)_3$, and each $R^5$ is independently $C_1$-$C_8$ alkyl or phenyl.

2. A complex in accordance with claim 1 wherein each $R^5$ is H.

3. A complex in accordance with claim 2 wherein $R^4$ is $CH_3$.

4. A complex in accordance with claim 3 wherein each $R^5$ is a methyl group.

5. A complex in accordance with claim 1 wherein $R^2$ is H.

6. A complex in accordance with claim 5 wherein both $R^1$ and $R^3$ are $CF_3$.

7. A complex in accordance with claim 1 wherein $R^4-C\equiv C-Si(R^5)_3$ represents bis(trimethylsilyl)acetylene.

* * * * *